(12) United States Patent
Ooban et al.

(10) Patent No.: US 9,332,906 B2
(45) Date of Patent: May 10, 2016

(54) OPHTHALMOLOGIC IMAGING APPARATUS AND OPHTHALMOLOGIC IMAGING METHOD

(75) Inventors: Hideyuki Ooban, Kawaguchi (JP); Yasuhiro Nakahara, Kawasaki (JP); Hiroshi Itoh, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 142 days.

(21) Appl. No.: 13/119,635

(22) PCT Filed: Jun. 10, 2010

(86) PCT No.: PCT/JP2010/003884
§ 371 (c)(1),
(2), (4) Date: Mar. 17, 2011

(87) PCT Pub. No.: WO2010/143443
PCT Pub. Date: Dec. 16, 2010

(65) Prior Publication Data
US 2011/0170063 A1 Jul. 14, 2011

(30) Foreign Application Priority Data

Jun. 11, 2009 (JP) .................................. 2009-140270
Jun. 7, 2010 (JP) .................................. 2010-130294

(51) Int. Cl.
*A61B 3/14* (2006.01)
*A61B 3/00* (2006.01)

(52) U.S. Cl.
CPC ........................................ *A61B 3/14* (2013.01)

(58) Field of Classification Search
USPC ................................................. 351/206, 246
See application file for complete search history.

(56) References Cited

U.S. PATENT DOCUMENTS

| 4,436,388 A | 3/1984 | Takahashi |
| 2002/0047989 A1 | 4/2002 | Shibata |
| 2007/0146535 A1 | 6/2007 | Nanjo |

FOREIGN PATENT DOCUMENTS

| JP | 60-207636 | 10/1985 |
| JP | H02-99032 | 4/1990 |
| JP | H02-099032 A | 4/1990 |
| JP | H02-268733 A | 11/1990 |
| JP | 07-008457 A | 1/1995 |
| JP | 8-256988 A | 10/1996 |
| JP | 9-066030 A | 3/1997 |
| JP | 09-289973 A | 11/1997 |
| JP | 10-043139 A | 2/1998 |
| JP | 2008-035944 A | 2/2008 |

OTHER PUBLICATIONS

Japanese Patent Office Notification of Reason for Refusal for JP Patent Application No. 2013-149571, Sep. 24, 2014.

*Primary Examiner* — Jack Dinh
(74) *Attorney, Agent, or Firm* — Canon U.S.A., Inc., IP Division

(57) ABSTRACT

An ophthalmologic imaging apparatus that captures an image of a subject's eye is provided. The apparatus includes a focusing unit configured to focus light returned from the subject's eye that is illuminated by the light of a first wavelength, onto an imaging unit, and a moving unit configured to move the focusing unit based on an optical path length difference between the light of the first wavelength and the light of a second wavelength that is different from the first wavelength when light returned from the subject's eye that is illuminated by the light of the second wavelength is focused onto the imaging unit.

71 Claims, 11 Drawing Sheets

OPHTHALMOLOGIC IMAGING APPARATUS AND OPHTHALMOLOGIC IMAGING METHOD

TECHNICAL FIELD

The present invention relates to ophthalmologic imaging apparatuses and ophthalmologic imaging methods for capturing an image of a subject's eye.

BACKGROUND ART

Fundus cameras that capture images of the fundus of a subject's eye include mydriatic fundus cameras and non-mydriatic fundus cameras. The mydriatic fundus cameras observe a subject's eye in which mydriatic drops are put using visible light and capture an image of the subject's eye. The non-mydriatic fundus cameras observe a subject's eye in which mydriatic drops are not put using near-infrared light and capture an image of the subject's eye. Further, there have been provided mydriatic and non-mydriatic fundus cameras that have functions of the mydriatic fundus cameras and the non-mydriatic fundus cameras. For example, Japanese Patent Application Laid-Open No. 9-66030 describes a mydriatic and non-mydriatic fundus camera that observes a subject's eye into which mydriatic drops are put using visible light by using an optical finder as means for observing a moving image. In this technology, when observing a subject's eye into which mydriatic drops are not put using near-infrared light, the optical path of reflected light from the fundus is changed to an optical path different from the path in the case of the observation of the subject's eye into which the mydriatic drops are put. The reflected light is guided to a charge-coupled device (CCD) that is image capturing means for a still image.

Further, Japanese Patent Application Laid-Open No. 8-256988 discusses a mydriatic and non-mydriatic fundus camera that is downsized using only one image capturing means. The technology of the No. 8-256988 discusses an optical element for optical path length correction that corrects an optical path difference generated due to a difference between the wavelengths of used light. The optical element is arranged in an optical path to a television camera that is an image capturing means.

Japanese Patent Application Laid-Open No. 10-43139 discusses a device that has image capturing means for capturing an image using reflected light from the fundus of an eye illuminated by visible light or infrared light. In the device, a bypass optical path for correcting an optical path length of the reflected light to the image capturing means is provided.

CITATION LIST

Patent Literature

PTL 1: Japanese Patent Application Laid-Open No. 9-66030
PTL 2: Japanese Patent Application Laid-Open No. 8-256988
PTL 3: Japanese Patent Application Laid-Open No. 10-43139

SUMMARY OF INVENTION

The present invention is based on an assumption that a common imaging unit is used to capture an image using light that has different wavelengths (observation light and photographing light). By the use of a focusing unit for focusing on the imaging unit, as compared to the technology discussed in Japanese Patent Application Laid-Open No. 9-66030, smaller, lighter, and simple-structured apparatuses having fewer components and novel structure can be provided.

According to an aspect of the present invention, an ophthalmologic imaging apparatus that captures an image of a subject's eye is provided. The apparatus includes a focusing unit configured to focus light returned from the subject's eye that is illuminated by the light of a first wavelength, onto an imaging unit, and a moving unit configured to move the focusing unit based on an optical path length difference between the light of the first wavelength and the light of a second wavelength that is different from the first wavelength when light returned from the subject's eye that is illuminated by the light of the second wavelength is focused onto the imaging unit.

According to another aspect of the present invention, an ophthalmologic imaging method for capturing an image of a subject's eye is provided. The method includes irradiating the subject's eye with the light of a first wavelength, focusing onto an imaging unit based on an optical path length difference between the light of the first wavelength and the light of a second wavelength that is different from the first wavelength, and irradiating the subject's eye with the light of the second wavelength.

According to another aspect of the present invention, an ophthalmologic imaging apparatus that captures an image of a subject's eye is provided. The apparatus includes an illumination optical system configured to irradiate the subject's eye with the light of a first wavelength and the light of a second wavelength that is different from the first wavelength, a photographing optical system having a focusing unit configured to focus light returned from the subject's eye that is illuminated by the illumination optical system onto an imaging unit, and a moving unit configured to move the focusing unit based on an optical path length difference between the light of the first wavelength and the light of the second wavelength.

According to the above-described ophthalmologic imaging apparatuses and ophthalmologic imaging method, the smaller, lighter, and simply structured apparatuses having fewer components and novel structure than before can be provided.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

Figure 1A:
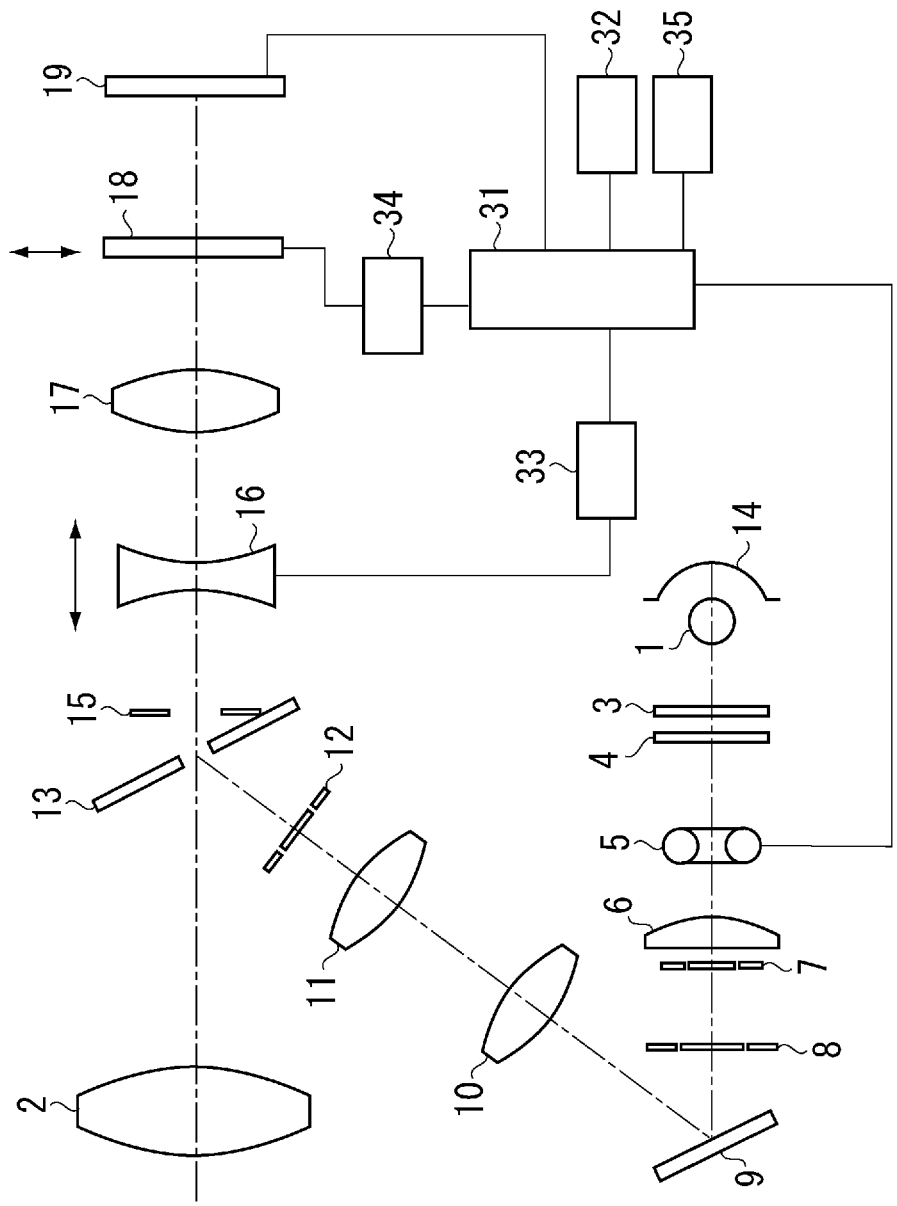
FIG. 1A is a view illustrating structure of fundus camera according to first and second exemplary embodiment of the present invention.

FIG. 1A is a view illustrating a structure of a non-mydriatic fundus camera according to an exemplary embodiment of the present invention. From an observation light source 1 that includes a halogen lamp to an objective lens 2 that faces a subject's eye is an illumination optical system. In the illumination optical system, the observation light source 1, a visible cut filter 3, a diffusion plate 4, a photographic light source 5 that comprises xenon tubes, a lens 6, a diaphragm 7, an eye-lens diaphragm 8, and a mirror 9 are arranged. In the reflecting direction of the mirror 9, relay lenses 10 and 11, a cornea stop 12, and a perforated mirror 13 are arranged in order. At the back of the observation light source 1, a reflecting mirror 14 is provided.

Figure 2A:
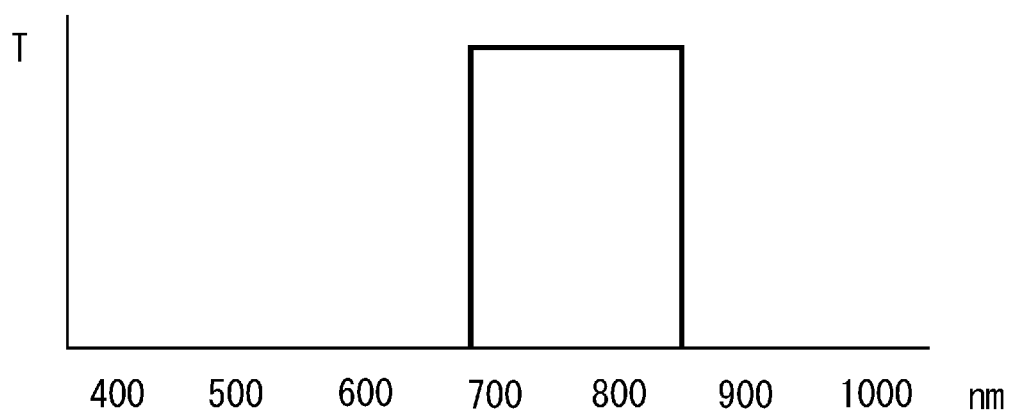
FIG. 2A illustrates characteristics of each wavelength band.

FIG. 2A illustrates transmission characteristics of the visible cut filter 3. The visible cut filter 3 does not pass light of visible wavelengths and passes light of near-infrared wavelengths of 680 nm or above.

At the back of the perforated mirror 13, an observation and photographing optical system is arranged. In the optical system, a photographic diaphragm 15, a focus lens 16 that can move along an optical path, an imaging lens 17, a near-infrared cut filter 18 that can be inserted into and removed from the optical path, and an image capturing unit 19 are arranged. The image capturing unit 19 has sensitivity ranging from visible light to near-infrared light that is invisible, and can output moving images and still images.

An output signal of the image capturing unit 19 is connected to a control unit (also referred to as display control unit) 31 and a monitor (also referred to as display unit) 32. An output signal of the control unit 31 is connected to the photographic light source 5, the focus lens 16 via a driving unit 33, and the near-infrared cut filter 18 (hereinafter, filters that select a wavelength of light for focusing on the image capturing unit may be referred to as wavelength selection units) via a driving unit 34. To the control unit 31, a photographing switch 35 for still image photographing is connected.

In moving image observation, light flux from the observation light source 1 passes through the visible cut filter 3 and is obtained as a near-infrared wavelength. The wavelength is used as illumination light (also referred to as light of a first wavelength). By the illumination light, a fundus of a subject's eye is illuminated. The image of the subject's eye is formed on an imaging surface of the image capturing unit 19 by the observation and photographing optical system. During the operation, the near-infrared cut filter 18 is retracted from the optical path by the driving unit 34. The operator performs positioning such that the fundus is positioned at a desired point while observing the moving image output from the image capturing unit 19 with the monitor 32. Then, in a state where the fundus and the image capturing unit 19 are conjugate to each other with respect to position, the control unit 31 controls the focus lens 16 through the driving unit 33 to perform focusing operation.

Figure 2B:
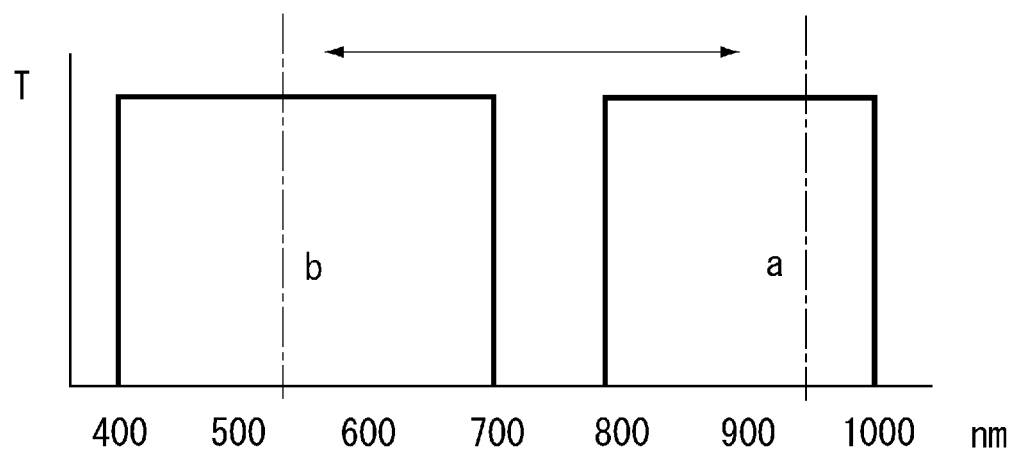
FIG. 2B illustrates characteristics of each wavelength band.

When capturing the image, as illumination light (also referred to as light of a second wavelength), visible light from the photographic light source 5 is used. When the photographing switch 35 is pressed, at a position where the focus lens 16 is being driven, the control unit 31 performs the focusing operation through the driving unit 33. At the same time, the photographic light source 5 emits light, and the control unit 31 inserts the near-infrared cut filter 18 into the observation and photographing optical system through the driving unit 34. Then, the image capturing unit 19 captures a still image, and the captured fundus image is displayed on the monitor 32. The control unit 31 stores an amount of movement of the focus lens 16 corresponding to an optical path difference between an arbitrary wavelength within a near-infrared wavelength range a of around 780 to 1000 nm and an arbitrary wavelength within a visible wavelength range b of around 400 to 700 nm shown in FIG. 2B. When the shooting is performed, the control unit 31 further moves the focus lens 16 by the stored amount from the in-focus position at the observation through the driving unit 33.

When the still image capturing ends, in order to return to the moving image observation, the control unit 31 moves back the focus lens 16 by the above-described amount via the driving unit 33 and retracts the near-infrared cut filter 18 from the optical path via the driving unit 34. The driving control of the focus lens 16 by the control unit 31 is not limited to the automatic focusing.

Figure 1B:
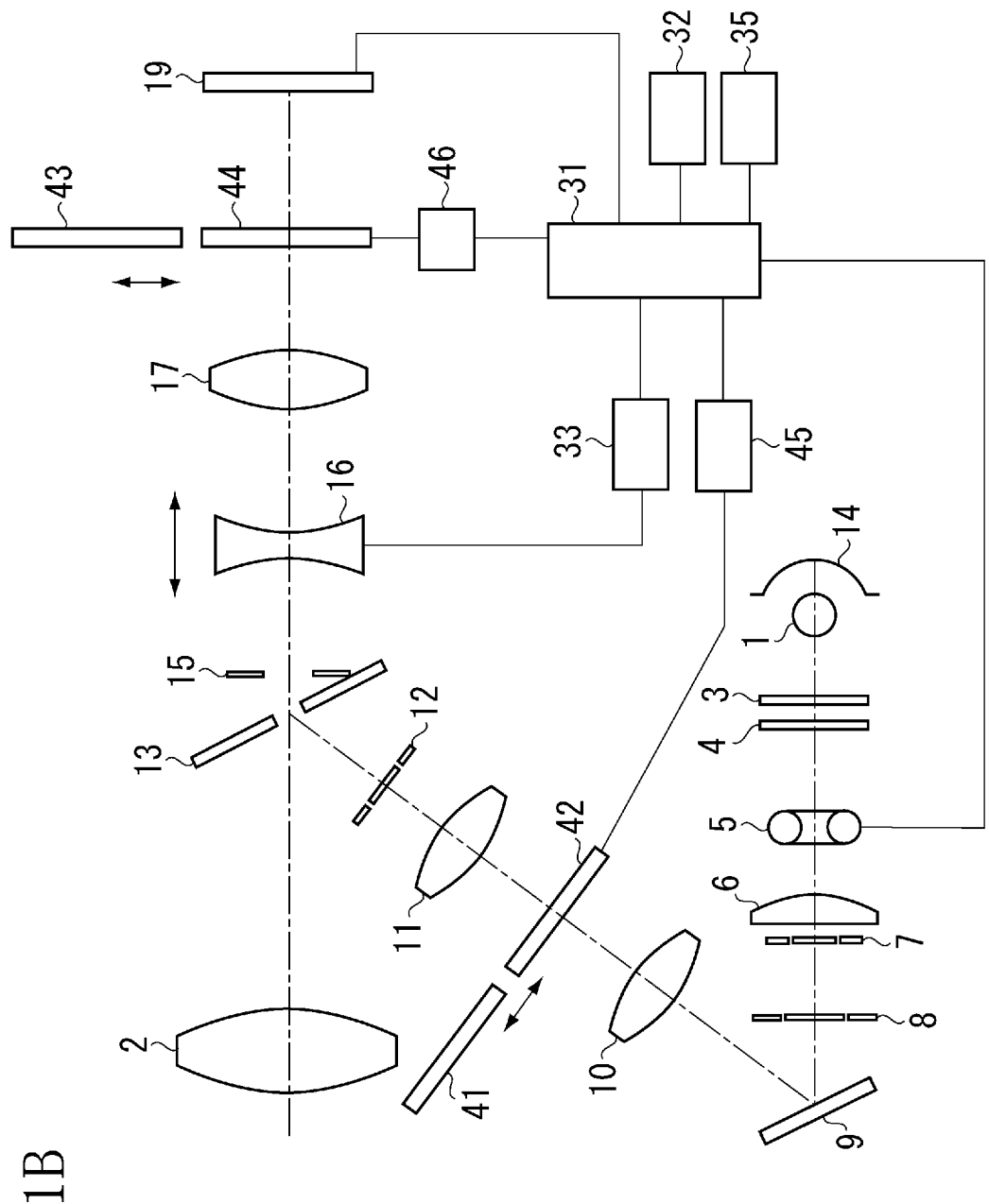
FIG. 1B is a view illustrating structure of fundus camera according to first and second exemplary embodiment of the present invention.

FIG. 1B illustrates a structure of a fundus camera that can perform autofluorescence photographing according to the second exemplary embodiment of the present invention. Reference numerals the same as those in the drawing used in the above-described description represent the same components. Between the relay lenses 10 and 11, an autofluorescence excitation filter 41 and an optical path length correction glass 42, which can be inserted into and removed from the optical path, are arranged so that they can be switched. Between the imaging lens 17 and the image capturing unit 19, an autofluorescence bandpass filter 43 and an optical path length correction glass 44 are arranged so that they can be switched. Output of the control unit 31 is connected to the autofluorescence excitation filter 41 and the optical path length correction glass 42 through a driving unit 45, and also connected to the autofluorescence bandpass filter 43 and the optical path length correction glass 44 through the driving unit 46.

Figure 3A:
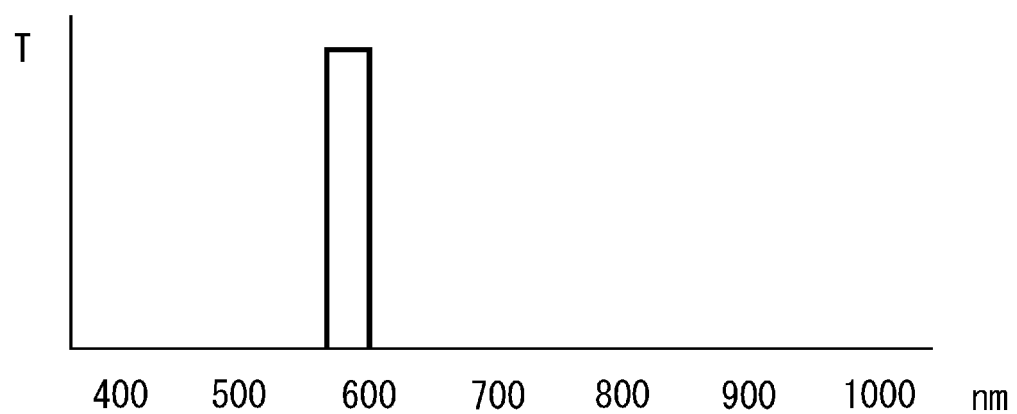
FIG. 3A illustrates transmission characteristics of each filter.
Figure 3B:
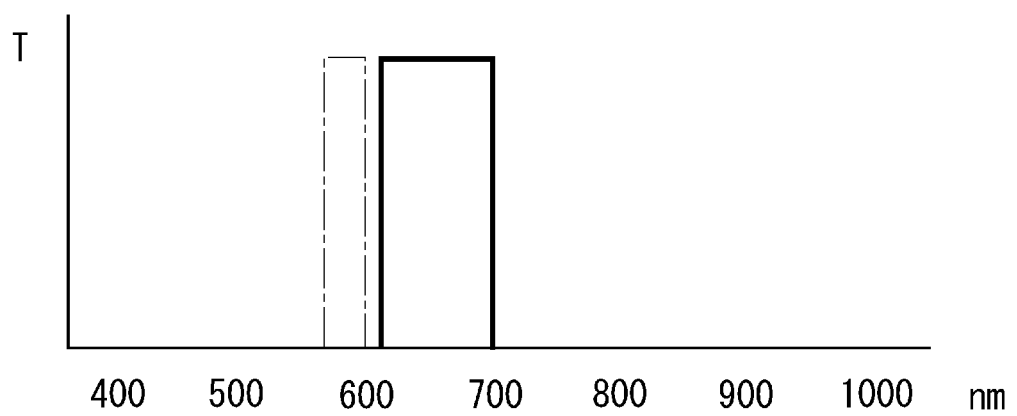
FIG. 3B illustrates transmission characteristics of each filter.

FIG. 3A illustrates transmission characteristics of the autofluorescence excitation filter 41. The autofluorescence excitation filter 41 transmits wavelengths of around 580 nm and blocks the other wavelengths. FIG. 3B illustrates transmission characteristics of the autofluorescence bandpass filter 43. The autofluorescence bandpass filter 43 transmits wavelengths of around 620 to 700 nm and blocks the other wavelengths. In FIG. 3B, the dotted line shows the transmission characteristics of the autofluorescence excitation filter 41 in FIG. 3A. It shows that the transmission band in FIG. 3B does not overlap with the transmission band of the autofluorescence bandpass filter 43.

To observe an moving image, as illumination light, near-infrared light is used similarly to the above-described exemplary embodiment. In the illumination optical system, the control unit 31 inserts the optical path length correction glass 42 into the optical path through the driving unit 45. In the observation and photographing optical system, the control unit 31 inserts the optical path length correction glass 44 into the optical path through the driving unit 46.

The operator performs positioning such that the image of the fundus is positioned at a desired point while observing the moving image output from the image capturing unit 19 with the monitor 32. Then, the control unit 31 controls the focus lens 16 through the driving unit 33 to perform focusing operation.

To photograph a still image, as illumination light, visible light from the photographic light source 5 is used. When the photographing switch 35 is pressed, in synchronization with the shooting, in the illumination optical system, the control unit 31 switches the optical path length correction glass 42 to the autofluorescence excitation filter 41 via the driving unit 46. In the observation and photographing optical system, the control unit 31 switches the optical path length correction glass 44 to the autofluorescence bandpass filter 43 via the driving unit 46 in synchronization with the shooting, the control unit 31 performs focusing control of the focus lens 16. Simultaneously, the photographic light source 5 emits light and still image photographing is performed. The image captured as an autofluorescence image generated at the fundus is displayed on the monitor 32.

Figure 2C:
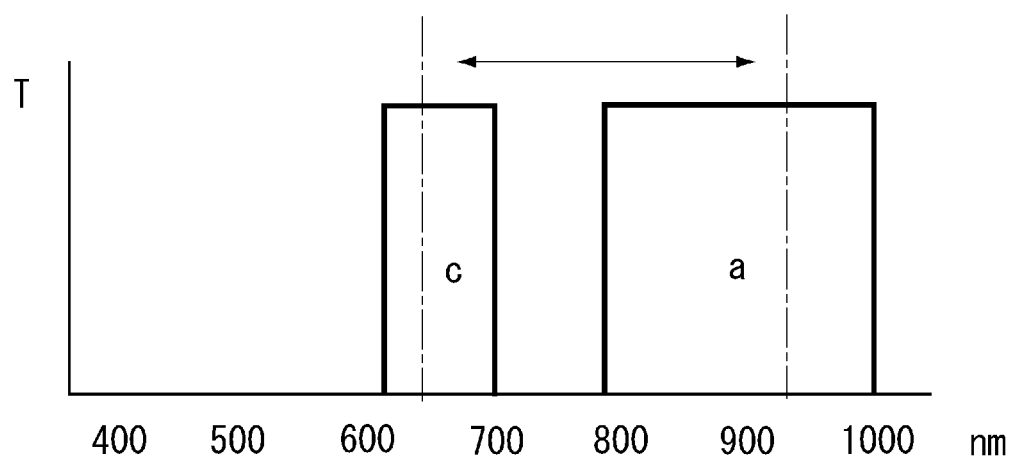
FIG. 2C illustrates characteristics of each wavelength band.

An optical path difference is generated due to a difference between a wavelength within the near-infrared wavelength range a of about 780 to 1000 nm and a wavelength within an autofluorescence fluorescence wavelength range c of about 620 to 700 nm shown in FIG. 2C. The control unit 31 stores a movement amount of the focus lens 16 corresponding to the optical path difference. In synchronization with the shooting, the control unit 31 moves the focus lens 16 by the movement amount.

When the still image photographing ends, in order to return to the moving image observation, in the illumination optical system, the control unit 31 switches the autofluorescence excitation filter 41 to the optical path length correction glass 42. In the observation and photographing optical system, the control unit 31 retracts the autofluorescence bandpass filter 43 and moves back the focus lens 16 by the movement amount.

When the shooting is performed using visible light, the near-infrared filter can be provided at a desired position in the illumination optical system or the observation and photographing optical system, and the thickness of the optical filter is not limited to a certain thickness.

In a fundus camera according to the third exemplary embodiment of the present invention, the visible cut filter 3 in front of the observation light source 1 is removed from FIG. 1B. By the configuration, illumination light from the observation light source 1 selectively includes visible light.

To observe a moving image, as illumination light (also referred to as light of a first wavelength), visible light is used. In the illumination optical system, the control unit 31 performs control to insert the optical path length correction glass 42 into the optical path via the driving unit 45. In the observation and photographing optical system, the control unit 31 performs control to insert the optical path length correction glass 44 into the optical path via the driving unit 46.

The operator performs positioning such that the image of the fundus is positioned at a desired point while observing the moving image output from the image capturing unit 19 with the monitor 32. Then, the control unit 31 drives the focus lens 16 to perform focusing operation.

To photograph a still image, as illumination light (also referred to as light of a second wavelength), visible light is used. When the photographing switch 35 is pressed, in the illumination optical system, the control unit 31 switches the optical path length correction glass 42 to the autofluorescence excitation filter 41 via the driving unit 45. In the observation and photographing optical system, the control unit 31 switches the optical path length correction glass 44 to the autofluorescence bandpass filter 43 via the driving unit 46. Further, in synchronization with the shooting, the control unit 31 performs control to move the focus lens 16. Simultaneously, the photographic light source 5 emits light and the still image photographing is performed. The captured image is displayed on the monitor 32.

Figure 2D:
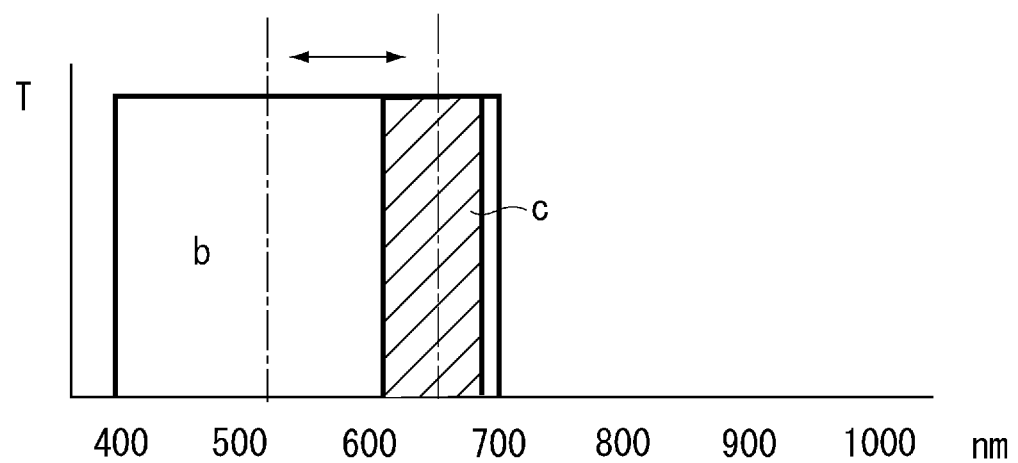
FIG. 2D illustrates characteristics of each wavelength band.

The control unit 31 stores a movement amount corresponding to an optical path difference generated due to a difference between a wavelength within the visible wavelength range b of around 400 to 700 nm and a wavelength within the autofluorescence fluorescence wavelength range c of around 620 to 700 nm shown in FIG. 2D. In synchronization with the shooting, the control unit 31 moves the focus lens 16 by the stored movement amount.

When the still image photographing ends, in order to return to the moving image observation, the control unit 31 switches the autofluorescence excitation filter 41 to the optical path length correction glass 42. Further, the control unit 31 switches the autofluorescence bandpass filter 43 to the optical path length correction glass 44 and moves back the focus lens 16 by the stored movement amount.

A fundus camera according to the fourth exemplary embodiment of the present invention includes an infrared fluorescent (ICG (Indocyanine green)) excitation filter 51 and an infrared fluorescent (ICG) bandpass filter 53 in replace of the autofluorescence excitation filter 41 and the autofluorescence bandpass filter 43 illustrated in FIG. 1B respectively.

Between the imaging lens 17 and the image capturing unit 19, the infrared fluorescent (ICG) bandpass filter 53 and the optical path length correction glass 44 are arranged so that they can be switched. The infrared fluorescent excitation filter 51 and the optical path length correction glass 42 are driven in response to an instruction by the control unit 31 by the driving unit 45. The infrared fluorescent bandpass filter 53 and the optical path length correction glass 44 are driven by the driving unit 46.

Figure 3C:
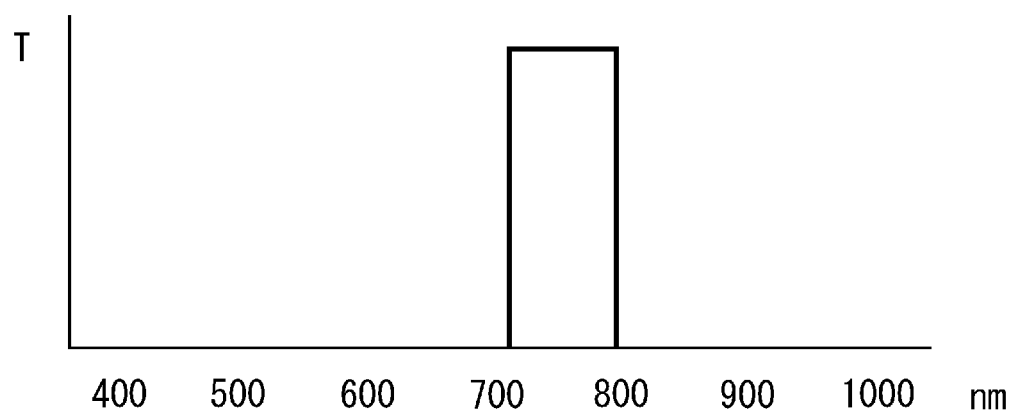
FIG. 3C illustrates transmission characteristics of each filter.
Figure 3D:
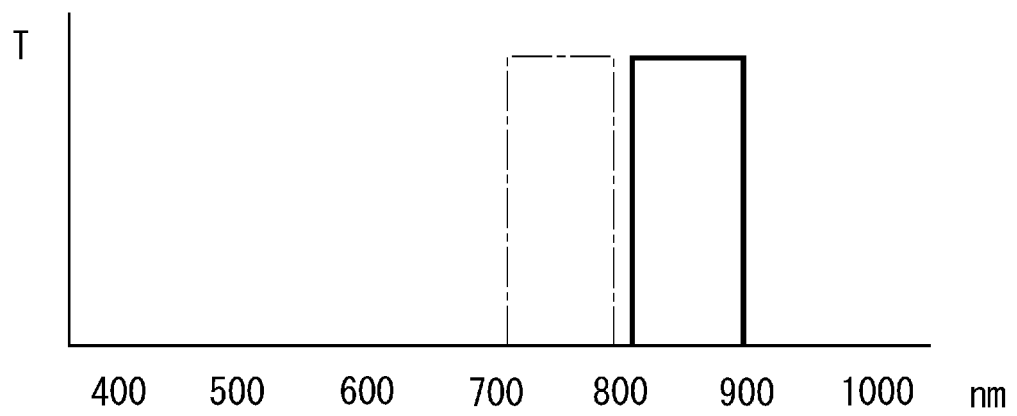
FIG. 3D illustrates transmission characteristics of each filter.

FIG. 3C illustrates transmission characteristics of the infrared fluorescent excitation filter 51. The infrared fluorescent excitation filter 51 transmits wavelengths of around 720 to 800 nm and blocks the other wavelengths. FIG. 3D illustrates transmission characteristics of the infrared fluorescent bandpass filter 53. The infrared fluorescent (ICG) bandpass filter 53 transmits wavelengths of around 820 to 900 nm and blocks the other wavelengths. The dotted line shows the transmission characteristics of the infrared fluorescent excitation filter 51 in FIG. 3D. It shows that the transmission band in FIG. 3D does not overlap with the transmission band of the infrared fluorescent bandpass filter 53.

To observe a moving image, near-infrared wavelength is used as illumination light. In the illumination optical system, the control unit 31 inserts the optical path length correction glass 42 into the optical path via the driving unit 45. In the observation and photographing optical system, the control unit 31 inserts the optical path length correction glass 44 via the driving unit 46.

The operator performs positioning such that the image of the fundus is positioned at a desired point while observing the moving image output from the image capturing unit 19 with the monitor 32. Then, the control unit 31 drives the focus lens 16 to perform focusing operation.

To observe a still image, visible wavelength is used as illumination light. When the photographing switch 35 is pressed, in the illumination optical system, the control unit 31 switches the optical path length correction glass 42 to the infrared fluorescent excitation filter 51 via the driving unit 45.

In the observation and photographing optical system, the control unit 31 switches the optical path length correction glass 44 to the infrared fluorescent bandpass filter 53 via the driving unit 46. Further, in synchronization with the shooting, the control unit 31 performs focusing control of the focus lens 16. Simultaneously, the photographic light source 5 emits light and the still image photographing is performed. The captured image is displayed on the monitor 32.

Figure 2E:
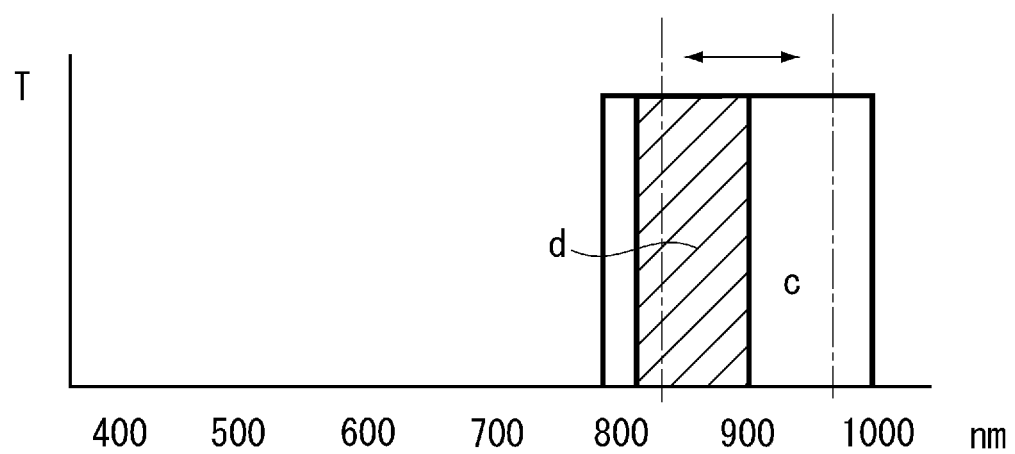
FIG. 2E illustrates characteristics of each wavelength band.

The control unit 31 stores a movement amount corresponding to an optical path difference generated due to a difference between a wavelength within the near-infrared wavelength range a of around 780 to 1000 nm and a wavelength within an infrared fluorescence fluorescence wavelength range d of around 820 to 900 nm shown in FIG. 2E. In synchronization with the shooting, the control unit 31 moves the focus lens 16 by the movement amount.

When the still image photographing ends, in order to return to the moving image observation, the control unit 31 switches the infrared fluorescent excitation filter 51 to the optical path length correction glass 42. Further, the control unit 31 switches the infrared fluorescent bandpass filter 53 to the optical path length correction glass 44. Further, the control unit 31 moves back the focus lens 16 to the original position by the movement amount.

In the above-described exemplary embodiments of the present invention, a dichroic mirror that can be inserted into and removed from the observation and photographing optical path can be used to correct the optical path when a light flux splitting unit for optical path splitting is inserted or retracted.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Applications No. 2009-140270 filed Jun. 11, 2009 and No. 2010-130294 filed Jun. 7, 2010, which are hereby incorporated by reference herein in their entirety.

The invention claimed is:

1. An ophthalmologic imaging apparatus that captures an image of a subject's eye, the apparatus comprising:
a focusing unit configured to focus a first return light returned from the subject's eye that is illuminated by an observation light of a first wavelength, onto an imaging unit;
a moving unit configured to move the focusing unit along an optical path;
an optical member that is insertable into and removable from the optical path; and
a control unit configured to control, when an image of the subject's eye is captured by the imaging unit using a second return light returned from the subject's eye that is illuminated by photographing light of a second wavelength that is different from the first wavelength, the moving unit based on an optical path length difference between a wavelength of the first return light and a wavelength of the second return light, wherein the optical path length difference is caused by inserting the optical member into or removing the optical member from the optical path.

2. The ophthalmologic imaging apparatus according to claim 1, having an arrangement in which the subject's eye and the imaging unit are conjugate to each other in a case where the light returned from the subject's eye that is illuminated by the light of the first and second wavelengths is focused onto the imaging unit.

3. The ophthalmologic imaging apparatus according to claim 1, further comprising:
an illumination optical system configured to irradiate the subject's eye with the light of the first and second wavelengths.

4. The ophthalmologic imaging apparatus according to claim 1, further comprising:
an observation light source that generates near-infrared light or visible light that contains the light of the first wavelength;
a photographing light source that generates visible light that contains the light of the second wavelength,
wherein, after the subject's eye is observed using the observation light source and the focusing unit is moved by the moving unit, the image of the subject's eye is captured using the photographing light source.

5. The ophthalmologic imaging apparatus according to claim 1, wherein the focusing unit further comprises a focus lens that can move along the optical path.

6. The ophthalmologic imaging apparatus according to claim 1, further comprising:
a display control unit configured to display a moving image or a still image generated based on an output signal from the imaging unit, on a display unit,
wherein, in response to completion of an image capturing of the subject's eye, the moving unit moves the focusing unit to a position at which the light of the first wavelength is focused and the display control unit displays the moving image on the display unit.

7. The ophthalmologic imaging apparatus according to claim 1, further comprising:
a wavelength selection unit configured to select the wavelength of the light to be focused on the imaging unit, wherein the control unit is configured to control the wavelength selection unit to be inserted into or removed from the optical path.

8. The ophthalmologic imaging apparatus according to claim 1, further comprising:
an autofluorescence excitation filter configured to be insertable into and removable from an optical path for illumination of the observation light; and
an autofluorescence bandpass filter configured to be insertable into and removable from an optical path of the second return light,
wherein, in a case where an autofluorescence image of the subject's eye is photographed using the second return light after the first return light is focused onto the imaging unit, the autofluorescence excitation filter and the autofluorescence bandpass filter to be inserted into the optical path.

9. The opthalmologic imaging apparatus according to claim 8,
wherein the first wavelength is composed of two different wavelength bands, and
wherein, in the two different wavelength bands, positioning is performing such that the image of the fundus is positioned at a desired point while observing.

10. The opthalmologic imaging apparatus according to claim 9,
wherein the first wavelength is composed of a near-infrared wavelength range and a visible wavelength range.

11. The ophthalmologic imaging apparatus according to claim 9,
further comprising a near-infrared cut filter that is inserted into and removed from an optical path of an illumination optical system for illuminating the subject's eye in order to change a wavelength range between the two different wavelength ranges.

12. The ophthalmologic imaging apparatus according to claim 1,
further comprising a photographing signal inputting unit configured to input a photographing signal for performing photographing of the subject's eye using the photographing light, wherein the control unit is configured to control the moving unit to move the focusing unit in response to an input of the photographing signal.

13. The ophthalmologic imaging apparatus according to claim 1,
wherein the control unit is configured to control the moving unit to move the focusing unit based on a movement amount corresponding to an optical path difference generated due to a difference between the first wavelength and the second wavelength.

14. The ophthalmologic imaging apparatus according to claim 1,
wherein the control unit is configured to control the moving unit to move the focusing unit based on an optical path difference between the light returned from the subject's eye that is illuminated by the light of the first wavelength and the light returned from the subject's eye that is illuminated by the light of the second wavelength.

15. The ophthalmologic imaging apparatus according to claim 1,
wherein the control unit is configured to control the moving unit to move the focusing unit along the optical path by a movement amount corresponding to the optical path length difference after the first return light is focused onto the imaging unit by the focusing unit and before an image of the subject's eye is captured by the imaging unit using the second return light.

16. The ophthalmologic imaging apparatus according to claim 1, further comprising: an obtaining unit configured to obtain a moving image of the subject's eye by the imaging unit using the first return light, and to obtain a still image of the subject's eye by the imaging unit using the second return light after the focusing unit is moved by the moving unit.

17. The ophthalmologic imaging apparatus according to claim 16, further comprising: a display control unit configured to display the moving image on a display unit and to display the still image on the display unit after the still image is obtained.

18. The ophthalmologic imaging apparatus according to claim 1,
wherein the first wavelength is within an infrared wavelength range,
wherein the second wavelength is within a visible wavelength range, and
wherein the imaging unit has sensitivity to light at least within the infrared wavelength range and the visible wavelength range.

19. The ophthalmologic imaging apparatus according to claim 1,
wherein the control unit is configured to control the moving unit to move the focusing unit back to an original position in response to end of photographing the subject's eye.

20. The ophthalmologic imaging apparatus according to claim 1, further comprising:
a light flux splitting unit configured to be insertable into and removable from an optical path of the focusing unit,
wherein the control unit is configured to control the moving unit to move the focusing unit along the optical path so that the optical path is corrected based on the optical path with the light flux splitting unit inserted therein in a case where the light flux splitting unit is retracted from the optical path.

21. The ophthalmologic imaging apparatus according to claim 1, wherein the moving unit is configured to move the focusing unit along the optical path by a moving amount different between in a case where autofluorescence photographing is performed on the subject's eye and in a case where photographing other than the autofluorescence photographing is performed on the subject's eye.

22. The ophthalmologic imaging apparatus according to claim 1,
wherein the control unit is configured to control, when the image of the subject's eye is captured by the imaging unit, the moving unit to move the focusing unit along the optical path so as to correct the optical path length difference.

23. The ophthalmologic imaging apparatus according to claim 1, wherein the optical member is a wavelength selection filter that is insertable into and removable from the optical path of a photographing optical system for photographing the subject's eye, and
wherein the optical path length difference is caused by inserting the wavelength selection filter into the optical path.

24. The ophthalmologic imaging apparatus according to claim 1, wherein the optical member is a dichroic mirror that is insertable into and removable from an optical path of a photographing optical system for photographing the subject's eye, and
wherein the optical path length difference is caused by removing the dichroic mirror from the optical path.

25. The ophthalmologic imaging apparatus according to claim 1, wherein the optical member is an autofluorescence bandpass filter that is insertable into and removable from the optical path of a photographing optical system for photographing the subject's eye, and
wherein the optical path length difference is caused by inserting the autofluorescence bandpass filter into the optical path.

26. The ophthalmologic imaging apparatus according to claim 1, wherein the optical member is a first filter and a second filter that is selectively insertable into and removable from the optical path of a photographing optical system for photographing the subject's eye, and
wherein the optical path length difference is caused by inserting the first filter into the optical path and removing the second filter from the optical path.

27. A method for controlling an ophthalmologic imaging apparatus that includes a focusing unit configured to focus a first return light returned from the subject's eye that is illuminated by an observation light of a first wavelength onto an imaging unit, a moving unit configured to move the focusing unit along an optical path, and an optical member that is insertable into and removable from the optical path, the method comprising:

controlling, when an image of the subject's eye is captured by the imaging unit using a second return light returned from the subject's eye that is illuminated by photographing light of a second wavelength that is different from the first wavelength, the moving unit based on an optical path length difference between a wavelength of the first return light and a wavelength of the second return light, wherein the optical path length difference is caused by inserting the optical member into or removing the optical member from the optical path.

28. The method according to claim 27,
wherein the subject's eye and the imaging unit are conjugate to each other in a case where the light returned from the subject's eye that is illuminated by the light of the first and second wavelengths is focused onto the imaging unit.

29. The method according to claim 27,
wherein the moving unit is controlled to move the focusing unit along the optical path by a movement amount corresponding to the optical path length difference after the first return light is focused onto the imaging unit by the focusing unit and before an image of the subject's eye is captured by the imaging unit using the second return light.

30. The method according to claim 27,
wherein the moving unit is controlled to move the focusing unit in response to an input of a photographing signal for photographing the subject's eye using the photographing light.

31. The method according to claim 27,
further comprising: obtaining a moving image of the subject's eye by the imaging unit using the first return light, and obtaining a still image of the subject's eye by the imaging unit using the second return light after the focusing unit is moved by the moving unit.

32. The method according to claim 31,
further comprising: displaying the moving image on a display unit and displaying the still image on the display unit after the still image is obtained.

33. The method according to claim 27,
wherein the first wavelength is within an infrared wavelength range,
wherein the second wavelength is within a visible wavelength range, and
wherein the imaging unit has sensitivity to light at least within the infrared wavelength range and the visible wavelength range.

34. The ophthalmologic imaging method according to claim 27, further comprising: inserting
an autofluorescence excitation filter configured to be insertable into and removable from an optical path for illumination of the observation light, and
an autofluorescence bandpass filter configured to be insertable into and removable from an optical path of the second return light in a case where an autofluorescence image of the subject's eye is photographed using the second return light after the first return light is focused onto the imaging unit.

35. The method according to claim 27,
wherein the moving unit is controlled to move the focusing unit back to an original position in response to end of photographing the subject's eye.

36. The ophthalmologic imaging method according to claim 27,
wherein the focusing unit is moved along the optical path by a moving amount different between in a case where autofluorescence photographing is performed on the subject's eye and in a case where photographing other than the autofluorescence photographing is performed on the subject's eye.

37. The method according to claim 27, wherein the moving unit is controlled, when the image of the subject's eye is captured by the imaging unit, to move the focusing unit along the optical path so as to correct the optical path length difference.

38. The method according to claim 27, wherein the optical member is a wavelength selection filter that is insertable into and removable from the optical path of a photographing optical system for photographing the subject's eye, and wherein the optical path length difference is caused by inserting the wavelength selection filter into the optical path.

39. The method according to claim 27, wherein the optical member is a dichroic minor that is insertable into and removable from the optical path of a photographing optical system for photographing the subject's eye, and
wherein the optical path length difference is caused by removing the dichroic mirror from the optical path.

40. The method according to claim 27, wherein the optical member is an autofluorescence bandpass filter that is insertable into and removable from the optical path of a photographing optical system for photographing the subject's eye, and
wherein the optical path length difference is caused by inserting the autofluorescence bandpass filter into the optical path.

41. The method according to claim 27, wherein the optical member is a first filter and a second filter that is selectively insertable into and removable from the optical path of a photographing optical system for photographing the subject's eye, and
wherein the optical path length difference is caused by inserting the first filter into the optical path and removing the second filter from the optical path.

42. A non-transitory computer-readable storage medium having program code thereon to perform a method of controlling an ophthalmologic imaging apparatus that includes a focusing unit configured to focus a first return light returned from the subject's eye that is illuminated by an observation light of a first wavelength onto an imaging unit, a moving unit configured to move the focusing unit along an optical path, and an optical member that is insertable into and removable from the optical path, the method comprising:

controlling, when an image of the subject's eye is captured by the imaging unit using a second return light returned from the subject's eye that is illuminated by photographing light of a second wavelength that is different from the first wavelength of the first return light and a wavelength of the second return light, wherein the optical path length difference is caused by inserting the optical member into or removing the optical member from the optical path.

43. The non-transitory computer readable storage medium according to claim 42,
wherein the moving unit is controlled, when the image of the subject's eye is captured by the imaging unit, to move the focusing unit along the optical path so as to correct the optical path length difference.

44. The non-transitory computer readable storage medium according to claim 42,
wherein the optical member is a wavelength selection filter that is insertable into and removable from the optical path of a photographing optical system for photographing the subject's eye, and
wherein the optical path length difference is caused by inserting the wavelength selection filter into the optical path.

45. The non-transitory computer readable storage medium according to claim 42,
wherein the optical member is a dichroic mirror that is insertable into and removable from the optical path of a photographing optical system for photographing the subject's eye, and
wherein the optical path length difference is caused by removing the dichroic mirror from the optical path.

46. The non-transitory computer readable storage medium according to claim 42,
wherein the optical member is an autofluorescence bandpass filter that is insertable into and removable from the optical path of a photographing optical system for photographing the subject's eye, and
wherein the optical path length difference is caused by inserting the autofluorescence bandpass filter into the optical path.

47. The non-transitory computer readable storage medium according to claim 42,
wherein the optical member is a first filter and a second filter that is selectively insertable into and removable from the optical path of a photographing optical system for photographing the subject's eye, and
wherein the optical path length difference is caused by inserting the first filter into the optical path and removing the second filter from the optical path.

48. An ophthalmologic imaging apparatus comprising:
a focusing unit configured to focus a first return light returned from a subject's eye that is illuminated by an observation light of a first wavelength, onto an imaging unit; and
a moving unit configured to move the focusing unit along an optical path so that the first return light is focused onto the imaging unit, and before an image of the subject's eye is captured by the imaging unit using a second return light returned from the subject's eye that is illuminated by observation light of a second wavelength different from the first wavelength and after the focusing unit is moved along the optical path so that the first return light is focused onto the imaging unit, to move the focusing unit along the optical path by a moving amount corresponding to an optical path length difference between a wavelength of the first return light and a wavelength of the second return light.

49. The ophthalmologic imaging apparatus according to claim 48,
wherein the moving unit is configured to move the focusing unit along the optical path by a moving amount different between in a case where autofluorescence photographing is performed on the subject's eye and in a case where photographing other than the autofluorescence photographing is performed on the subject's eye.

50. The ophthalmologic imaging apparatus according to claim 48,
wherein the first wavelength is within an infrared wavelength range,
wherein the second wavelength is within a visible wavelength range, and
wherein the imaging unit has sensitivity to light at least within the infrared wavelength range and the visible wavelength range.

51. The ophthalmologic imaging apparatus according to claim 48, further comprising:
a wavelength selection unit configured to select the wavelength of the light to be focused on the imaging unit; and
a control unit configured to control the wavelength selection unit to be inserted into or removed from the optical path.

52. The ophthalmologic imaging apparatus according to claim 48, further comprising:
an autofluorescence excitation filter configured to be insertable into and removable from an optical path for illumination of the observation light;
an autofluorescence bandpass filter configured to be insertable into and removable from an optical path of the second return light; and
a control unit configured to control , in a case where an autofluorescence image of the subject's eye is photographed using the second return light after the first return light is focused onto the imaging unit, the autofluorescence excitation filter and the autofluorescence bandpass filter to be inserted into the optical path.

53. The ophthalmologic imaging apparatus according to claim 48, further comprising:
a light flux splitting unit configured to be insertable into and removable from an optical path of the focusing unit; and
a control unit configured to control the moving unit to move the focusing unit along the optical path so that the optical path is corrected based on the optical path with the light flux splitting unit inserted therein in a case where the light flux splitting unit is retracted from the optical path.

54. An ophthalmologic imaging method comprising:
moving a focusing unit along an optical path so that a first return light returned from a subject's eye that is illuminated by an observation light of a first wavelength is focused onto an imaging unit; and
moving, before an image of the subject's eye is captured by the imaging unit using a second return light returned from the subject's eye that is illuminated by observation light of a second wavelength different from the first wavelength and after the firstly moving the focusing unit, the focusing lens along the optical path by a moving amount corresponding to an optical path length difference between a wavelength of the first return light and a wavelength of the second return light.

55. The ophthalmologic imaging method according to claim 54, wherein the focusing unit is moved along the optical path by a moving amount different between in a case where autofluorescence photographing is performed on the subject's eye and in a case where photographing other than the autofluorescence photographing is performed on the subject's eye.

56. A non-transitory computer readable storage medium having program code thereon to cause an ophthalmologic imaging apparatus to perform an ophthalmologic imaging method comprising:
moving a focusing unit along an optical path so that a first return light returned from a subject's eye that is illuminated by an observation light of a first wavelength is focused onto an imaging unit; and
moving, before an image of the subject's eye is captured by the imaging unit using a second return light returned from the subject's eye that is illuminated by an observation light of a second wavelength different from the first wavelength and after the firstly moving the focusing unit, the focusing lens along the optical path by a moving amount corresponding to an optical path length difference between a wavelength of the first return light and a wavelength of the second return light.

57. An ophthalmologic imaging apparatus comprising:
an illumination unit configured to illuminate a subject's eye;
a focusing unit configured to focus a return light returned from the subject's eye that is illuminated by the illumination unit;
a moving unit configured to move the focusing unit along an optical path; and
a control unit configured to control the moving unit to move the focusing unit along the optical path by a moving amount corresponding to an optical path length difference between a wavelength of a first return light returned from the subject's eye that is illuminated by observation light and a wavelength of a second return light returned from the subject's eye that is illuminated by photographing light in synchronization with photographing the subject's eye,
wherein the control unit is configured to control the moving unit to move the focusing unit along the optical path by a moving amount different between in a case where autofluorescence photographing is performed on the subject's eye and in a case where photographing other than the autofluorescence photographing is performed on the subject's eye.

58. The ophthalmologic imaging apparatus according to claim 57,
wherein the first wavelength is within an infrared wavelength range,
wherein the second wavelength is within a visible wavelength range, and
wherein the imaging unit has sensitivity to light at least within the infrared wavelength range and the visible wavelength range.

59. A method of controlling an ophthalmologic imaging apparatus including an illumination unit configured to illuminate a subject's eye, a focusing unit configured to focus a return light returned from the subject's eye that is illuminated by the illumination unit, and a moving unit configured to move the focusing unit along an optical path, the method comprising:
controlling the moving unit to move the focusing unit along the optical path by a moving amount corresponding to an optical path length difference between a wavelength of the first return light returned from the subject's eye that is illuminated by observation light and a wavelength of a second return light returned from the subject's eye that is illuminated by photographing light in synchronization with photographing the subject's eye
wherein the moving unit is controlled to move the focusing unit along the optical path by a moving amount different between in a case where autofluorescence photographing is performed on the subject's eye and in a case where photographing other than the autofluorescence photographing is performed on the subject's eye.

60. A non-transitory computer readable storage medium having program code thereon to perform a method of controlling an ophthalmologic imaging apparatus including an illumination unit configured to illuminate a subject's eye, a focusing unit configured to focus a return light returned from the subject's eye that is illuminated by the illumination unit, and a moving unit configured to move the focusing unit along an optical path, the method comprising:
controlling the moving unit to move the focusing unit along the optical path by a moving amount corresponding to an optical path length difference between a wavelength of the first return light returned from the subject's eye that is illuminated by observation light and a wavelength of a second return light returned from the subject's eye that is illuminated by photographing light in synchronization with photographing the subject's eye
wherein the moving unit is controlled to move the focusing unit along the optical path by a moving amount different between in a case where autofluorescence photographing is performed on the subject's eye and in a case where photographing other than the autofluorescence photographing is performed on the subject's eye.

61. An ophthalmologic imaging apparatus comprising:
an illumination unit configured to illuminate a subject's eye;
a focusing unit configured to focus a return light returned from the subject's eye that is illuminated by the illumination unit;
a moving unit configured to move the focusing unit along an optical path; and
a control unit configured to control the moving unit to move the focusing unit along the optical path by a moving amount corresponding to an optical path length difference between a wavelength of the first return light returned from the subject's eye that is illuminated by observation light and a wavelength of a second return light returned from the subject's eye that is illuminated by photographing light when photographing the subject's eye is finished,
wherein the control unit is configured to control the moving unit to move the focusing unit along the optical path by a moving amount different between in a case where autofluorescence photographing is performed on the subject's eye and in a case where photographing other than the autofluorescence photographing is performed on the subject's eye.

62. The ophthalmologic imaging apparatus according to claim 61,
wherein the first wavelength is within an infrared wavelength range,
wherein the second wavelength is within a visible wavelength range, and
wherein the imaging unit has sensitivity to light at least within the infrared wavelength range and the visible wavelength range.

63. A method of controlling an ophthalmologic imaging apparatus including an illumination unit configured to illuminate a subject's eye, a focusing unit configured to focus a return light returned from the subject's eye that is illuminated by the illumination unit, and a moving unit configured to move the focusing unit along an optical path, the method comprising:
controlling the moving unit to move the focusing unit along the optical path by a moving amount corresponding to an optical path length difference between a wavelength of the first return light returned from the subject's eye that is illuminated by observation light and a wavelength of a second return light returned from the subject's eye that is illuminated by photographing light when photographing the subject's eye is finished,
wherein the moving unit is controlled to move the focusing unit along the optical path by a moving amount different between in a case where autofluorescence photographing is performed on the subject's eye and in a case where photographing other than the autofluorescence photographing is performed on the subject's eye.

64. A non-transitory computer readable storage medium having program code thereon to perform a method of controlling an ophthalmologic imaging apparatus including an illumination unit configured to illuminate a subject's eye, a focusing unit configured to focus a return light returned from the subject's eye that is illuminated by the illumination unit, and a moving unit configured to move the focusing unit along an optical path, the method comprising:

controlling the moving unit to move the focusing unit along the optical path by a moving amount corresponding to an optical path length difference between a wavelength of the first return light returned from the subject's eye that is illuminated by observation light and a wavelength of a second return light returned from the subject's eye that is illuminated by photographing light when photographing the subject's eye is finished, wherein the moving unit is controlled to move the focusing unit along the optical path by a moving amount different between in a case where autofluorescence photographing is performed on the subject's eye and in a case where photographing other than the autofluorescence photographing is performed on the subject's eye.

65. An ophthalmologic imaging apparatus that captures an image of a subject's eye, the apparatus comprising:

a focusing unit configured to focus a first return light returned from the subject's eye that is illuminated by an observation light of a first wavelength, onto an imaging unit;

a moving unit configured to move, when an image of the subject's eye is captured by the imaging unit using a second return light returned from the subject's eye that is illuminated by photographing light of a second wavelength that is different from the first wavelength, the focusing unit along an optical path based on an optical path length difference between a wavelength of the first return light and a wavelength of the second return light;

a wavelength selection unit configured to select the wavelength of the light to be focused on the imaging unit; and a control unit configured to control the wavelength selection unit to be inserted into or removed from the optical path.

66. The ophthalmologic imaging apparatus according to claim 65, further comprising:

an autofluorescence excitation filter configured to be insertable into and removable from an optical path for illumination of the observation light; and an autofluorescence bandpass filter configured to be insertable into and removable from an optical path of the second return light, wherein the control unit configured to control, in a case where an autofluorescence image of the subject's eye is photographed using the second return light after the first return light is focused onto the imaging unit, the autofluorescence excitation filter and the autofluorescence bandpass filter to be inserted into the optical path.

67. The ophthalmologic imaging apparatus according to claim 65, further comprising:

a light flux splitting unit configured to be insertable into and removable from the optical path of the focusing unit; and a control unit configured to control the moving unit to move the focusing unit along the optical path so that the optical path is corrected based on the optical path with the light flux splitting unit inserted therein in a case where the light flux splitting unit is retracted from the optical path.

68. The ophthalmologic imaging apparatus according to claim 65, wherein the first wavelength is within an infrared wavelength range, wherein the second wavelength is within a visible wavelength range, and wherein the imaging unit has sensitivity to light at least within the infrared wavelength range and the visible wavelength range.

69. An ophthalmologic imaging method for capturing an image of a subject's eye, the method comprising:

focusing, by a focusing unit, a first return light returned from the subject's eye that is illuminated by an observation light of a first wavelength, onto an imaging unit;

moving, when an image of the subject's eye is captured by the imaging unit using a second return light returned from the subject's eye that is illuminated by photographing light of a second wavelength that is different from the first wavelength, the focusing unit along an optical path based on an optical path length difference between a wavelength of the first return light and a wavelength of the second return light; and controlling a wavelength selection unit configured to select the wavelength of the light to be focused on the imaging unit to be inserted into or removed from the optical path.

70. The method according to claim 69, further comprising: inserting an autofluorescence excitation filter configured to be insertable into and removable from an optical path for illumination of the observation light and an autofluorescence bandpass filter configured to be insertable into and removable from an optical path of the second return light in a case where an autofluorescence image of the subject's eye is photographed using the second return light after the first return light is focused onto the imaging unit.

71. A non-transitory computer readable storage medium having program code thereon to cause an ophthalmologic imaging apparatus to perform an ophthalmologic imaging method, the method comprising:

focusing, by a focusing unit, a first return light returned from the subject's eye that is illuminated by an observation light of a first wavelength, onto an imaging unit;

moving, when an image of the subject's eye is captured by the imaging unit using a second return light returned from the subject's eye that is illuminated by photographing light of a second wavelength that is different from the first wavelength, the focusing unit along an optical path based on an optical path length difference between a wavelength of the first return light and a wavelength of the second return light; and controlling a wavelength selection unit configured to select the wavelength of the light to be focused on the imaging unit to be inserted into or removed from the optical path.

* * * * *